(12) United States Patent
Wu et al.

(10) Patent No.: US 8,871,155 B2
(45) Date of Patent: Oct. 28, 2014

(54) DEVICES FOR DETECTING ANALYTES IN FLUID SAMPLE

(75) Inventors: Yuzhang Wu, Zhejiang (CN); Yun Ling, Hangzhou (CN); Jielin Dai, Hangzhou (CN)

(73) Assignee: Alere Switzerland GmbH, Zug (CH)

( * ) Notice: Subject to any disclaimer, the term of this patent is extended or adjusted under 35 U.S.C. 154(b) by 173 days.

(21) Appl. No.: 12/095,325

(22) PCT Filed: Nov. 13, 2006

(86) PCT No.: PCT/CN2006/003028
§ 371 (c)(1),
(2), (4) Date: Nov. 18, 2008

(87) PCT Pub. No.: WO2007/062575
PCT Pub. Date: Jun. 7, 2007

(65) Prior Publication Data
US 2009/0226883 A1    Sep. 10, 2009

Related U.S. Application Data

(63) Continuation of application No. 11/293,864, filed on Dec. 1, 2005, now abandoned.

(30) Foreign Application Priority Data

Nov. 30, 2005  (CN) .......................... 2005 1 0128570

(51) Int. Cl.
*G01N 35/00* (2006.01)
*B01L 3/00* (2006.01)

(52) U.S. Cl.
CPC ....... *B01L 3/5023* (2013.01); *B01L 2300/0663* (2013.01); *G01N 2035/00108* (2013.01); *B01L 3/5029* (2013.01); *B01L 2200/027* (2013.01)

USPC .......... 422/401; 422/400; 422/402; 422/403; 422/68.1; 422/501

(58) Field of Classification Search
USPC ............. 422/56, 58, 102, 400, 401, 402, 403, 422/68.1, 501; 436/165
See application file for complete search history.

(56) References Cited

U.S. PATENT DOCUMENTS 3,896,974 A    7/1975  McIntosh
4,014,748 A    3/1977  Spinner et al.
(Continued)

FOREIGN PATENT DOCUMENTS

CN    1084045 A    3/1994
CN    1314593 A    9/2001
(Continued)

OTHER PUBLICATIONS

U.S. Appl. No. 60/233,739, filed Sep. 19, 2000, Tung et al.
(Continued)

*Primary Examiner* — Sam P Siefke
(74) *Attorney, Agent, or Firm* — DLA Piper LLP (US)

(57) ABSTRACT

A device for detecting the presence or amount of an analyte in a fluid sample and method thereof, comprises a sample collector and a receiving cup for receiving and holding the sample collector within the receiving cup. The sample collector contains a compressible absorbent member for collecting the fluid sample, and has a first position and a second, locked position within the receiving cup. The absorbent member is uncompressed in the first position and is compressed in the second, locked position. The sample collector or the receiving cup has at least one test element having reagents for detecting the presence or amount of the analyte in the fluid sample.

9 Claims, 4 Drawing Sheets

(56) References Cited

U.S. PATENT DOCUMENTS

| | | |
|---|---|---|
| 4,114,605 A | 9/1978 | McGhee et al. |
| 4,275,149 A | 6/1981 | Litman et al. |
| 4,299,916 A | 11/1981 | Litman et al. |
| 4,458,020 A | 7/1984 | Bohn et al. |
| 4,635,488 A | 1/1987 | Kremer |
| 4,768,238 A | 9/1988 | Kleinberg et al. |
| 4,771,486 A | 9/1988 | Gutierrez et al. |
| 4,817,632 A | 4/1989 | Schramm |
| 4,853,325 A | 8/1989 | Vodian et al. |
| 4,857,453 A | 8/1989 | Ullman et al. |
| 4,877,850 A | 10/1989 | Geibel et al. |
| 4,886,175 A | 12/1989 | Schlaudecker |
| 4,923,798 A | 5/1990 | LeMoine et al. |
| 4,955,745 A | 9/1990 | Vauquelin |
| 4,962,025 A | 10/1990 | Moldowan |
| 5,050,616 A | 9/1991 | Wolff et al. |
| 5,073,484 A | 12/1991 | Swanson et al. |
| 5,076,474 A | 12/1991 | Hansen |
| 5,119,831 A | 6/1992 | Robin et al. |
| 5,160,329 A | 11/1992 | Oxley |
| 5,170,799 A | 12/1992 | Nagase et al. |
| 5,185,127 A | 2/1993 | Vonk |
| 5,186,900 A | 2/1993 | Jensen et al. |
| 5,211,182 A | 5/1993 | Deutsch et al. |
| 5,234,001 A | 8/1993 | Goldstein et al. |
| 5,246,145 A | 9/1993 | Leoncavallo et al. |
| 5,252,496 A | 10/1993 | Kang et al. |
| 5,260,031 A | 11/1993 | Seymour |
| 5,261,572 A | 11/1993 | Strater |
| 5,275,785 A | 1/1994 | May et al. |
| 5,328,058 A | 7/1994 | Leoncavallo et al. |
| 5,334,502 A | 8/1994 | Sangha |
| 5,339,829 A | 8/1994 | Thieme et al. |
| 5,352,410 A | 10/1994 | Hansen et al. |
| 5,376,337 A | 12/1994 | Seymour |
| 5,380,492 A | 1/1995 | Seymour |
| 5,393,496 A | 2/1995 | Seymour |
| 5,415,994 A | 5/1995 | Imrich et al. |
| 5,416,000 A | 5/1995 | Allen et al. |
| 5,424,193 A | 6/1995 | Pronovost et al. |
| 5,479,937 A | 1/1996 | Thieme et al. |
| 5,494,646 A | 2/1996 | Seymour |
| 5,504,013 A | 4/1996 | Senior |
| 5,559,041 A | 9/1996 | Kang et al. |
| 5,573,009 A | 11/1996 | Thieme et al. |
| 5,573,099 A | 11/1996 | Church et al. |
| 5,602,040 A | 2/1997 | May et al. |
| 5,609,160 A | 3/1997 | Bahl et al. |
| 5,622,871 A | 4/1997 | May et al. |
| 5,654,162 A | 8/1997 | Guire et al. |
| 5,656,503 A | 8/1997 | May et al. |
| 5,679,535 A | 10/1997 | Joyce et al. |
| 5,686,315 A | 11/1997 | Pronovost et al. |
| 5,712,170 A | 1/1998 | Kouvonen et al. |
| 5,714,341 A | 2/1998 | Thieme et al. |
| 5,736,322 A | 4/1998 | Goldstein |
| 5,738,634 A | 4/1998 | Caillouette |
| 5,766,961 A | 6/1998 | Pawlak et al. |
| 5,770,460 A | 6/1998 | Pawlak et al. |
| 5,786,227 A | 7/1998 | Charlton |
| 5,786,228 A | 7/1998 | Charlton |
| 5,786,427 A | 7/1998 | Kijima et al. |
| 5,830,154 A | 11/1998 | Goldstein et al. |
| 5,830,410 A | 11/1998 | Thieme et al. |
| 5,877,028 A | 3/1999 | Kouvonen et al. |
| 5,910,122 A | 6/1999 | D'Angelo |
| 5,916,815 A | 6/1999 | Lappe |
| 5,920,122 A | 6/1999 | D'Angelo |
| 5,922,283 A | 7/1999 | Hsu |
| 5,935,764 A | 7/1999 | Schramm |
| 5,935,864 A | 8/1999 | Schramm |
| 5,965,453 A | 10/1999 | Skiffington et al. |
| 5,965,458 A | 10/1999 | Kouvonen et al. |
| 5,968,746 A | 10/1999 | Schneider |
| 5,976,895 A | 11/1999 | Cipkowski |
| 5,981,293 A | 11/1999 | Charlton |
| 5,981,300 A | 11/1999 | Moll et al. |
| 5,986,895 A | 11/1999 | Stewart et al. |
| 6,022,326 A | 2/2000 | Tatum et al. |
| 6,046,058 A | 4/2000 | Sun et al. |
| 6,102,872 A | 8/2000 | Doneen et al. |
| 6,136,610 A | 10/2000 | Polito et al. |
| 6,140,136 A | 10/2000 | Lee |
| 6,150,178 A | 11/2000 | Cesarczyk |
| 6,180,395 B1 | 1/2001 | Skiffington et al. |
| 6,183,972 B1 | 2/2001 | Kuo et al. |
| 6,187,268 B1 | 2/2001 | Albarella et al. |
| 6,187,269 B1 | 2/2001 | Lancesseur et al. |
| 6,187,598 B1 | 2/2001 | May et al. |
| 6,194,221 B1 | 2/2001 | Rehg et al. |
| 6,194,224 B1 | 2/2001 | Good et al. |
| 6,221,678 B1 | 4/2001 | Chandler |
| 6,223,947 B1 | 5/2001 | Bernard |
| 6,228,660 B1 | 5/2001 | May et al. |
| 6,235,241 B1 | 5/2001 | Catt et al. |
| 6,241,689 B1 | 6/2001 | Chard et al. |
| 6,248,598 B1 | 6/2001 | Bogema |
| 6,271,046 B1 | 8/2001 | Chandler |
| 6,277,587 B1 | 8/2001 | Lamster |
| 6,277,646 B1 | 8/2001 | Guirguis et al. |
| 6,291,178 B1 | 9/2001 | Schneider |
| 6,297,020 B1 | 10/2001 | Brock |
| 6,303,081 B1 | 10/2001 | Mink et al. |
| 6,306,642 B1 | 10/2001 | Nelson et al. |
| 6,316,205 B1 | 11/2001 | Guan et al. |
| 6,338,969 B1 | 1/2002 | Shareef et al. |
| 6,352,862 B1 | 3/2002 | Davis et al. |
| 6,368,873 B1 | 4/2002 | Chang et al. |
| 6,372,513 B1 | 4/2002 | Nguyen et al. |
| 6,372,514 B1 | 4/2002 | Lee |
| 6,372,515 B1 | 4/2002 | Casterlin et al. |
| 6,372,516 B1 | 4/2002 | Sun |
| 6,375,896 B1 | 4/2002 | Wuske et al. |
| 6,375,897 B1 | 4/2002 | Bachand |
| 6,379,620 B1 | 4/2002 | Tydings et al. |
| 6,391,652 B2 | 5/2002 | Okada et al. |
| 6,403,383 B1 | 6/2002 | Casterlin et al. |
| 6,418,606 B1 | 7/2002 | Bachand |
| 6,423,550 B1 | 7/2002 | Jenkins et al. |
| 6,429,026 B1 | 8/2002 | Pettersson et al. |
| 6,440,087 B1 | 8/2002 | Sangha |
| 6,443,892 B1 | 9/2002 | Kidwell |
| 6,464,939 B1 | 10/2002 | Bachand et al. |
| 6,468,474 B2 | 10/2002 | Bachand et al. |
| 6,485,982 B1 | 11/2002 | Charlton |
| 6,489,172 B1 | 12/2002 | Bachand et al. |
| 6,506,612 B2 | 1/2003 | Kang et al. |
| 6,514,768 B1 | 2/2003 | Guire et al. |
| 6,514,769 B2 | 2/2003 | Lee et al. |
| 6,528,323 B1 | 3/2003 | Thayer et al. |
| 6,537,823 B1 | 3/2003 | Smith |
| 6,548,019 B1 | 4/2003 | Lee et al. |
| 6,565,808 B2 | 5/2003 | Hudak et al. |
| 6,656,744 B2 | 12/2003 | Pronovost et al. |
| 6,669,908 B2 * | 12/2003 | Weyker et al. .................. 422/58 |
| 6,673,630 B2 | 1/2004 | Albarella et al. |
| 6,730,268 B2 | 5/2004 | Lee et al. |
| 6,780,160 B2 | 8/2004 | Zhou et al. |
| 6,887,681 B2 | 5/2005 | DiCesare et al. |
| 6,979,576 B1 | 12/2005 | Cheng et al. |
| 7,048,693 B2 | 5/2006 | Zhou et al. |
| 7,114,403 B2 | 10/2006 | Wu et al. |
| 7,270,959 B2 | 9/2007 | Hudak |
| 7,300,633 B2 | 11/2007 | Hudak et al. |
| 7,481,977 B2 | 1/2009 | Percival et al. |
| 7,517,495 B2 | 4/2009 | Wu et al. |
| 2001/0004532 A1 | 6/2001 | Chandler |
| 2001/0008614 A1 | 7/2001 | Aronowitz |
| 2001/0008774 A1 | 7/2001 | May et al. |
| 2001/0021536 A1 | 9/2001 | Lee |
| 2001/0023076 A1 | 9/2001 | Guan et al. |
| 2001/0023324 A1 | 9/2001 | Pronovost et al. |
| 2001/0041368 A1 | 11/2001 | May et al. |
| 2002/0001845 A1 | 1/2002 | Klaerner et al. |

(56) References Cited

U.S. PATENT DOCUMENTS

| | | | |
|---|---|---|---|
| 2002/0004019 A1* | 1/2002 | Bachand et al. | 422/58 |
| 2002/0015663 A1 | 2/2002 | Goldstein et al. | |
| 2002/0020713 A1 | 2/2002 | Kis et al. | |
| 2002/0031840 A1 | 3/2002 | Albarella et al. | |
| 2002/0031845 A1 | 3/2002 | Cipkowski | |
| 2002/0052050 A1 | 5/2002 | Douglas et al. | |
| 2002/0085953 A1 | 7/2002 | Parker | |
| 2002/0085958 A1 | 7/2002 | Nemcek et al. | |
| 2002/0098512 A1 | 7/2002 | Goodell et al. | |
| 2002/0132267 A1 | 9/2002 | Wong | |
| 2002/0132370 A1 | 9/2002 | Lassen et al. | |
| 2002/0137231 A1 | 9/2002 | Cipkowski | |
| 2002/0146346 A1 | 10/2002 | Konecke | |
| 2002/0150884 A1 | 10/2002 | Zmuda et al. | |
| 2002/0155028 A1 | 10/2002 | Wong | |
| 2002/0155029 A1 | 10/2002 | Mink et al. | |
| 2002/0173047 A1 | 11/2002 | Hudak et al. | |
| 2002/0192839 A1 | 12/2002 | Mink et al. | |
| 2003/0045003 A1 | 3/2003 | Smith | |
| 2003/0064526 A1 | 4/2003 | Niedbala et al. | |
| 2003/0129088 A1 | 7/2003 | Lee et al. | |
| 2003/0129673 A1 | 7/2003 | Schwarz et al. | |
| 2003/0138971 A1 | 7/2003 | D'Aurora | |
| 2003/0175992 A1 | 9/2003 | Toranto et al. | |
| 2003/0175993 A1 | 9/2003 | Toranto et al. | |
| 2003/0190259 A1 | 10/2003 | Alley | |
| 2003/0207466 A1 | 11/2003 | Po Lee | |
| 2004/0018636 A1 | 1/2004 | Zhou et al. | |
| 2004/0082878 A1 | 4/2004 | Baldwin et al. | |
| 2004/0184954 A1* | 9/2004 | Guo et al. | 422/56 |
| 2004/0191760 A1 | 9/2004 | Zhou et al. | |
| 2005/0119589 A1 | 6/2005 | Tung et al. | |
| 2005/0180882 A1 | 8/2005 | Tung et al. | |
| 2005/0202568 A1 | 9/2005 | Tung et al. | |
| 2006/0034728 A1 | 2/2006 | Kloepfer et al. | |
| 2006/0121548 A1 | 6/2006 | Robbins et al. | |
| 2006/0292035 A1* | 12/2006 | Gould et al. | 422/58 |
| 2007/0128070 A1 | 6/2007 | Wu et al. | |
| 2009/0117665 A1 | 5/2009 | Tung et al. | |
| 2009/0232702 A1 | 9/2009 | Wu et al. | |

FOREIGN PATENT DOCUMENTS

| | | |
|---|---|---|
| CN | 2476023 Y | 2/2002 |
| CN | 1603823 A | 4/2005 |
| CN | 1614383 A | 5/2005 |
| CN | 1645146 A | 7/2005 |
| EP | 0 390 984 A1 | 10/1990 |
| EP | 0 392 096 A1 | 10/1990 |
| EP | 0 455 916 A2 | 11/1991 |
| EP | 0 455 916 A3 | 11/1991 |
| EP | 0 500 172 A1 | 8/1992 |
| EP | 0 542 107 A1 | 5/1993 |
| EP | 0 561 322 A1 | 9/1993 |
| EP | 0 455 916 B1 | 2/1996 |
| EP | 0 734 684 A1 | 10/1996 |
| EP | 0 734 685 A1 | 10/1996 |
| EP | 0 734 686 A1 | 10/1996 |
| EP | 0 753 148 B1 | 12/1998 |
| EP | 1 216 931 A1 | 6/2002 |
| EP | 1 275 962 A1 | 1/2003 |
| EP | 1348960 A1 | 10/2003 |
| GB | 855916 | 12/1960 |
| JP | 11-304800 A | 11/1999 |
| WO | WO 92/16842 A1 | 10/1992 |
| WO | WO 93/11434 A1 | 6/1993 |
| WO | WO 94/07419 A1 | 4/1994 |
| WO | WO 94/18892 A1 | 9/1994 |
| WO | WO 95/02822 A1 | 1/1995 |
| WO | WO 95/07223 A2 | 3/1995 |
| WO | WO 95/07223 A3 | 5/1995 |
| WO | WO 95/27205 A1 | 10/1995 |
| WO | WO 97/20502 A1 | 6/1997 |
| WO | WO 98/44158 A1 | 10/1998 |
| WO | WO 99/06827 A2 | 2/1999 |
| WO | WO 99/06827 A3 | 4/1999 |
| WO | WO 99/22639 A1 | 5/1999 |
| WO | WO 99/22645 A1 | 5/1999 |
| WO | WO 99/27139 A1 | 6/1999 |
| WO | WO 99/50656 A1 | 10/1999 |
| WO | WO 00/15020 A1 | 3/2000 |
| WO | WO 00/20862 A1 | 4/2000 |
| WO | WO 00/25666 A1 | 5/2000 |
| WO | WO 00/64334 A1 | 11/2000 |
| WO | WO 01/08993 A1 | 2/2001 |
| WO | WO 01/81915 A1 | 11/2001 |
| WO | WO 01/49820 A1 | 12/2001 |
| WO | WO 02/04941 A2 | 1/2002 |
| WO | WO 02/07645 A2 | 1/2002 |
| WO | WO 02/04942 A1 | 2/2002 |
| WO | WO 02/16946 A2 | 2/2002 |
| WO | WO 02/04941 A3 | 4/2002 |
| WO | WO 02/07645 A3 | 5/2002 |
| WO | WO 02/058600 A2 | 8/2002 |
| WO | WO 02/059600 A2 | 8/2002 |
| WO | WO 02/082040 A2 | 10/2002 |
| WO | WO 02/096480 A2 | 12/2002 |
| WO | WO 02/16946 A3 | 1/2003 |
| WO | WO 02/082040 A3 | 1/2003 |
| WO | WO 02/059600 A3 | 3/2003 |
| WO | WO 02/96480 A3 | 3/2003 |
| WO | WO 02/058600 A3 | 3/2004 |
| WO | WO 2005/008216 A2 | 1/2005 |
| WO | WO 2005/050165 A2 | 6/2005 |
| WO | WO 2005/008216 A3 | 7/2005 |
| WO | WO 2005/050165 A3 | 7/2005 |
| WO | WO 2007/062575 A1 | 6/2007 |
| WO | WO 2008/012566 A2 | 1/2008 |
| WO | WO 2008/012566 A3 | 11/2008 |

OTHER PUBLICATIONS

International search report dated Jul. 19, 2006 for PCT Application No. US2004/038427.

International search report dated Feb. 1, 2007 for PCT Application No. CN2006/003028.

International search report dated Nov. 1, 2007 for PCT Application No. CN2007/70344.

International search report dated Mar. 16, 2009 for PCT Application No. IB2008/001831.

* cited by examiner

DEVICES FOR DETECTING ANALYTES IN FLUID SAMPLE

CROSS-REFERENCE TO RELATED APPLICATIONS

This application is a 35 USC §371 National Stage application of International Application No. PCT/CN2006/003028 filed Nov. 13, 2006, now expired; which is a continuation application of U.S. application Ser. No. 11/293,864 filed Dec. 1, 2005, now abandoned; which claims the benefit under 35 USC §119(a) to China Application Serial No. 200510128570.X filed Nov. 30, 2005. The disclosure of each of the prior applications is considered part of and is incorporated by reference in the disclosure of this application.

FIELD OF THE INVENTION

The present invention relates to a device and method for detecting the presence or amount of an analyte in a fluid sample.

BACKGROUND OF THE INVENTION

The following Background of the Invention is intended to aid the reader in understanding the invention and is not admitted to be prior art.

A variety of sample collection and test devices for clinical or home uses are available and described in the literature. For example, U.S. Pat. No. 5,376,337 discloses a saliva sampling device in which a piece of filter paper is used to collect saliva from a test subject's mouth and transfer the saliva to an indicator. U.S. Pat. Nos. 5,576,009 and 5,352,410 each disclose a syringe type fluid sampling device. In these devices, the collected fluid sample cannot be saved for confirmation testing at a later time after the initial result is obtained.

Many of other sample collection and test devices are inefficient in sample extraction from the collection device. Many of these devices are also very complex in their design and manufacture, and require the use of relatively expensive materials.

SUMMARY OF THE INVENTION

The present invention provides devices and methods for detecting the presence or amount of an analyte in a liquid sample. In one embodiment the liquid sample is saliva and the analyte is ethanol or a drug of abuse. The device can contain a sample collector and a receiving cup. The sample collector can contain an absorbent material configured so that the sample collector is conveniently placed into the mouth of a test subject. When the absorbent material has been filled with saliva, the sample collector is inserted into the receiving cup of the device, and placed into a locked position (e.g., by screwing the sample collector into the receiving cup). This causes the absorbent material to be compressed and sample to be extracted and moved onto a test element, which detects the presence or amount of the analyte of interest.

Thus, in a first aspect the present invention provides a device for detecting the presence or amount of an analyte in a fluid sample. The device has a sample collector containing a compressible absorbent member for collecting the fluid sample. The device also contains a receiving cup for receiving and holding the sample collector within the receiving cup. The sample collector has a first position and a second, locked position within the receiving cup, the absorbent member being uncompressed in the first position and being compressed and held within the cup in the second, locked position. The sample collector or the receiving cup also contains at least one test element having reagents for detecting the presence or amount of the analyte in the fluid sample. The test element is in fluid communication with the absorbent member when the sample collector is in the second, locked position.

In one embodiment the sample collector contains a test element holder housing the test element. The test element can be in fluid communication with the absorbent member through a passageway in the sample collector connecting the absorbent member and the test element. In one embodiment the absorbent pad is positioned between the passageway and the test element. The sample collector can have circumferential screw threads, and the receiving cup can have circumferential receiving threads. In one embodiment the screw threads and receiving threads are engaged when the sample collector is in the second, locked position.

In one embodiment the receiving cup is sealed from fluid communication with the exterior when the sample collector is in the second, locked position. In another embodiment the sample collector and the receiving cup are joined by a snap fit connection when the sample collector is in the second, locked position. The absorbent member can be a sponge suitable for placing in the mouth of a test subject, and the fluid sample can be saliva.

In one embodiment the sample collector has a flattened handle for manually gripping the sample collector, and the receiving cup contains the test element. The absorbent member can be in fluid communication with the test element through a passageway in the receiving cup when the sample collector is in the second, locked position.

In another aspect the present invention provides a device for detecting the presence or amount of an analyte in a fluid sample. The device contains a sample collector that has screw threads and a compressible absorbent member for collecting the fluid sample. The device also has a receiving cup for receiving and holding the sample collector within the receiving cup, and the receiving cup contains receiving threads. The sample collector has a first position within the receiving cup, and a second, locked position within the receiving cup where the screw threads and receiving threads are engaged. The absorbent member is uncompressed in the first position and is compressed and held within the cup in the second, locked position. The receiving cup is directly connected to a test element holder containing at least one test element, which has reagents for detecting the presence or amount of the analyte in the fluid sample. The test element is in fluid communication with the absorbent member when the sample collector is in the second, locked position.

In another aspect, the present invention provides methods for detecting the presence or amount of an analyte in a fluid sample. The methods involve using a device as disclosed herein. The steps include placing a volume of fluid sample in the absorbent member, inserting the sample collector into the receiving cup and moving the sample collector to the second, locked position, and determining the presence or amount of analyte in the fluid sample.

In one embodiment the fluid sample is saliva, and the saliva is placed in the absorbent member by placing the sample collector into the mouth of a test subject.

The summary of the invention described above is not limiting and other features and advantages of the invention will be apparent from the following detailed description, as well as from the claims.

DETAILED DESCRIPTION

Figure 1:
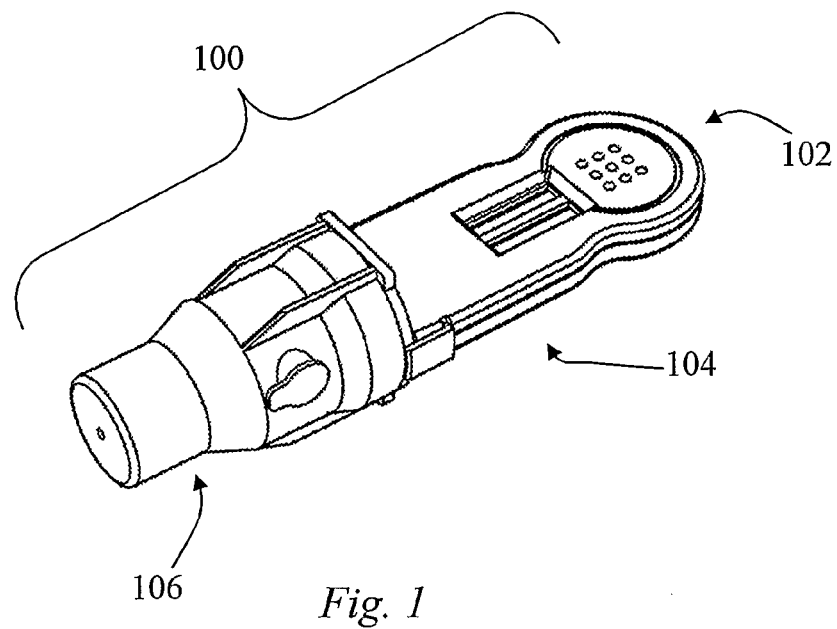
FIG. 1 is a perspective view of a device of the invention for detecting the presence or amount of an analyte in a fluid sample.

Referring to FIG. 1, a compact device 100 for detecting the presence or amount of an analyte in a fluid sample in accordance with a first embodiment of the present invention is illustrated in its assembled status. In the embodiment depicted in the Figures the device contains a flattened handle 102 for gripping the device, a sample collector portion 104 that contains a compressible absorbent member for collecting the fluid sample. The handle can take any convenient form or shape. Also illustrated is a receiving cup 106 for receiving and holding the sample collector. The embodiment in FIG. 1 is shown assembled, with the sample collector secured in a locked position within the receiving cup. The components of the device are conveniently formed out of molded plastic parts, but any suitable materials can be used. "Compressible" refers to the characteristic of a material where the shape of the material can be distorted by mechanical pressure so as to wring fluid from the material when the material is holding a fluid.

Figure 2:
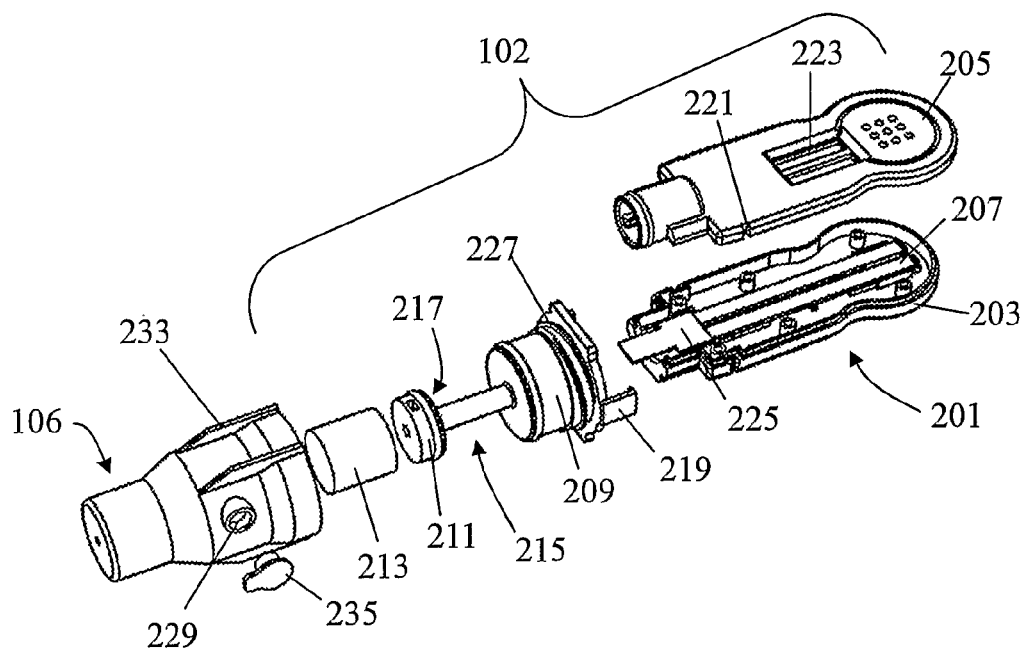
FIG. 2 is an exploded view of a device of the invention.
Figure 3:
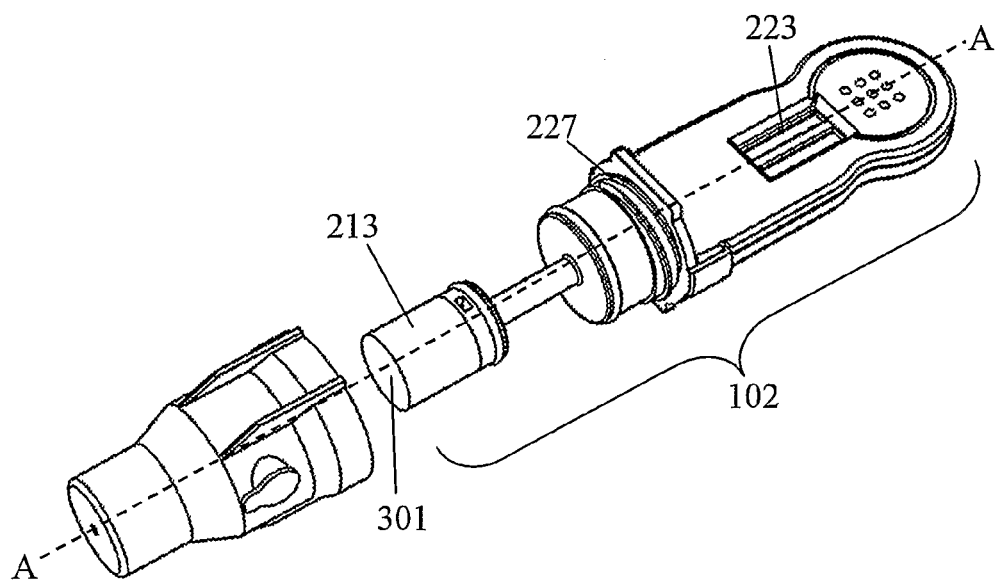
FIG. 3 is a perspective view of a device of the invention, where the sample collector is in the first position and the sample collector and receiving cup are separated.
Figure 4:
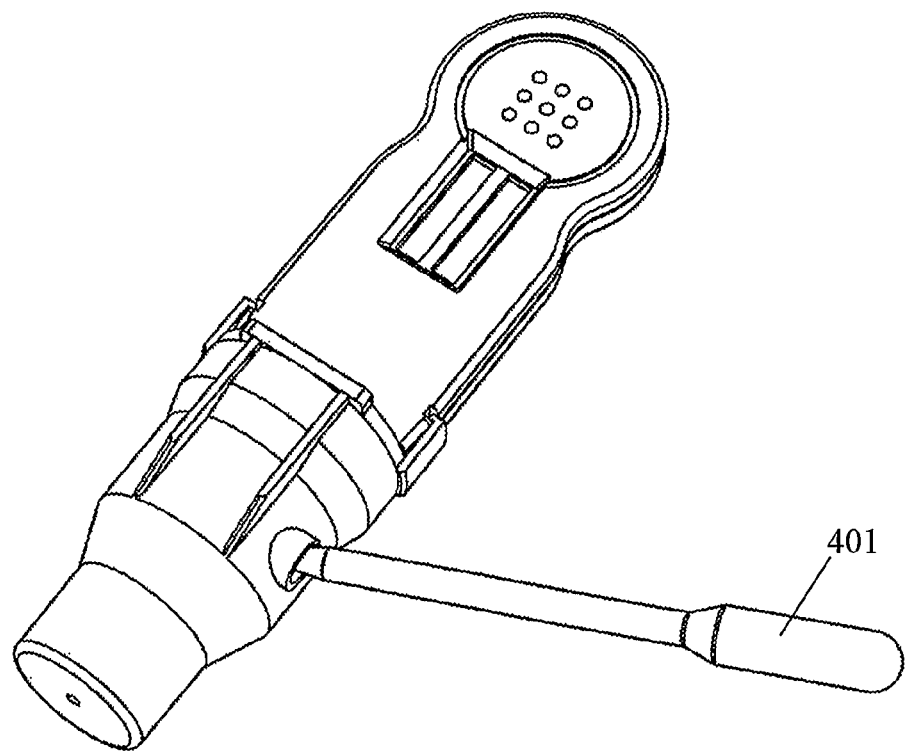
FIG. 4 is a perspective view of a device of the invention in the second, locked position. Illustrated is a procedure for extracting sample from a device that has previously been loaded with sample. In this embodiment sample is extracted from the sampling hole using a pipette.

In FIG. 2, the sample collector 102 is illustrated in an exploded view. A receiving cup 106 for receiving and holding the sample collector 102 therein is shown. The sample collector 102 has a lower casing 203 and an upper casing 205. In this embodiment the test element 207 is conveniently located inside the sample collector 102. A viewing window 223 can be included in the upper casing 205 to facilitate observation of the test result. In the embodiment depicted, a bibulous material 225 (e.g., filter paper) is situated between the outlet of the passageway 503 and the test element 207. The bibulous material 205 absorbs fluid released by the absorbent member 211 and transports it to the test element(s) 207, and therefore provides for fluid communication between the passageway and the test element. The device is designed so that the bibulous material 225 will not absorb and transport more fluid than can be loaded onto the test element without causing flooding of the test element. Excess fluid that reaches the bibulous material 225 passes through the outlet of the passageway 503 and is prevented from flowing to the test element 207 so as to prevent flooding of the test element 207. By structures being in "fluid communication" is meant that fluid passing from one structure will pass into the other with which it is in fluid communication. Thus, when the passageway is in fluid communication with the test element, fluid passing through the passageway passes through the bibulous material and into the test element. The passageway, bibulous material, and test element may make direct physical contact, or there may be a gap between them, but are retained in fluid communication. The absorbent member can be made of any material that absorbs and holds fluid. In one embodiment, the absorbent member is a sponge, but in other embodiments it can be an absorbent paper, nylon, cotton, or any other material that can absorb and hold fluid. A "bibulous material" is a material that absorbs and allows capillary transport of a fluid. Examples include, but are not limited to, filter paper or other types of absorbent paper, certain nylons, nitrocellulose, and other materials with the stated characteristics. With reference to the present disclosure the person of ordinary skill in the art will realize additional materials appropriate to form these structures.

In the embodiment depicted the sample collector 102 is formed by connecting the upper casing 205 and the lower casing 203 together, with the test element 207 and the bibulous material 205 housed inside the casings. In other embodiments the sample collector can be formed as a single solitary unit, or formed of other parts than those depicted here. In the embodiment depicted, snap tabs 219 are provided on the sample collector base 209, which mate with receiving holes 221 provided on the test element holder 102, thus securing the two parts together in this embodiment. In assembling the sample collector 102, the proximal end of the sample collector 102 is inserted into the open end of the sample collector base 209 and the snap tabs 219 are engaged with the corresponding receiving holes 221. In other embodiments, the snap tabs and receiving holes are replaced or supplemented by other suitable methods of joining the components, for example a screw connection, complementary parts that snap into place to secure the connection, or gluing, or any suitable method. In this embodiment, the upper casing 205 and the lower casing 207 are assembled to form a flattened handle for manually gripping the sample collector 201. Furthermore, the various parts of the device can be mated together by any convenient means. In various embodiments the parts can be mated as described above by using snap tabs or other parts that fit snuggly together, or by gluing, heat sealing, or any other suitable method.

The "test element" can be any assaying device that provides a detectable result. In some embodiments the test element is a test strip (e.g., a lateral flow test strip). The test strip can have specific binding molecules immobilized on the test strip and reagents for performing an immunoassay, such as a lateral flow assay. But in various other embodiments the test strip is configured with a chemical test, a biologically based test (e.g., an enzyme or ELISA assay), or a fluorescence-based assay. But in still other embodiments the test element can have other reagents necessary to conduct any suitable test that provides a detectable result. In one embodiment the test element contains reagents for detecting the presence of a drug of abuse. However, in other embodiments the test element can be any element that provides an indicator of the result of the assay. For example, a chemical or biological indicator can be utilized.

When the test element is a test strip, it can consist of a bibulous matrix (e.g., nitrocellulose) and/or other suitable materials. The matrix can have a sample loading zone, a reagent or label zone, and a detection zone. These types of test strips are known in the art and, with reference to the present disclosure, the person of ordinary skill will realize the variety of test strips that are useful in the present invention. In some embodiments a sample loading zone is present at one end of the test strip for the application of sample to the test strip. Reagents for conducting the assay or conditioning the sample can also be present at the sample loading zone, or they can be present in a separate reagent zone or label zone on the test strip. These reagents can serve a variety of purposes, for example preparing the sample for optimal binding with a specific binding molecule, or improving the stability of an analyte of interest.

The sample containing the analyte detected by the device can be any fluid sample. Examples of fluid samples suitable for testing with the present invention include oral fluid, saliva, whole blood, blood serum, blood plasma, urine, spinal fluid, biological swabs, mucus, and tissue. "Saliva" refers to the excretions of the salivary glands. "Oral fluid" is any fluid present in the buccal cavity.

The analyte whose presence or amount is detected can be any analyte for which a test element can be made. In one embodiment the analyte is a drug of abuse. Other examples of analytes of interest include a hormone, a protein, a peptide, a nucleic acid molecule, an etiological agent, and a specific binding pair member. A "drug of abuse" (DOA) is a drug that is taken for non-medicinal reasons (usually for mind-altering effects). The abuse of such drugs can lead to physical and mental damage and (with some substances) dependence, addiction and even death. Examples of DOAs include cocaine; amphetamines (e.g., black beauties, white bennies, dextroamphetamines, dexies, beans); methamphetamines (crank, meth, crystal, speed); barbiturates (Valium®, Roche Pharmaceuticals, Nutley, N.J.); sedatives (i.e. sleep-aids); lysergic acid diethylamide (LSD); depressants (downers, goofballs, barbs, blue devils, yellow jackets, ludes); tricyclic antidepressants (TCA, e.g., imipramine, amitriptyline and doxepin); phencyclidine (PCP); tetrahydrocannabinol (THC, pot, dope, hash, weed, etc.); and opiates (e.g., morphine, opium, codeine, heroin, oxycodone).

In the embodiment shown in the Figures, the sample collector 102 also contains a sample collector base 209. In this embodiment the sample collector base 209 has screw threads 211 to facilitate securing the sample collector 102 within the receiving cup 106 in a locked position. In this embodiment the sample collector 102 also has plunger head 211 for securing the absorbent member 213 to the sample collector 102, and an extender 215 for mounting the absorbent member at a position so that it is comfortable for the test subject to hold in the mouth. The absorbent member 213 can be made of absorbent material such as sponge or sponge-like material, or another material that has the capacity to absorb and hold liquid sample. When the absorbent material is a sponge, it can be of natural or synthetic origin. In the embodiment illustrated, the absorbent member 213 is a cylindrically-shaped sponge material suitable for placing into the mouth of a test subject to collect saliva. But in other embodiments the absorbent member can be of any suitable and convenient shape. In certain embodiments the absorbent member 213 is treated with a chemical component (e.g., citrate or another chemical) to promote the secretion of saliva. The absorbent member 213 can be affixed to the distal end of the extender 215 by any suitable means, for example, glue, epoxy, heat bonding or any other means that achieves a firm bonding or otherwise secures the absorbent member to the distal end of the extender. The extender 215 can also have a plunger head 217, to which the absorbent member 211 is bound.

In the embodiment depicted the sample collector base 209 is substantially barrel or cylindrically shaped and opens at its distal end to receive the proximal end of the test element holder 102. The parts of the sample collector base 209 and the test element holder 102 are conveniently designed to be complementary, and to be fitted together by any suitable means, such as by snapping together or by gluing, or any other suitable method.

Figure 5:
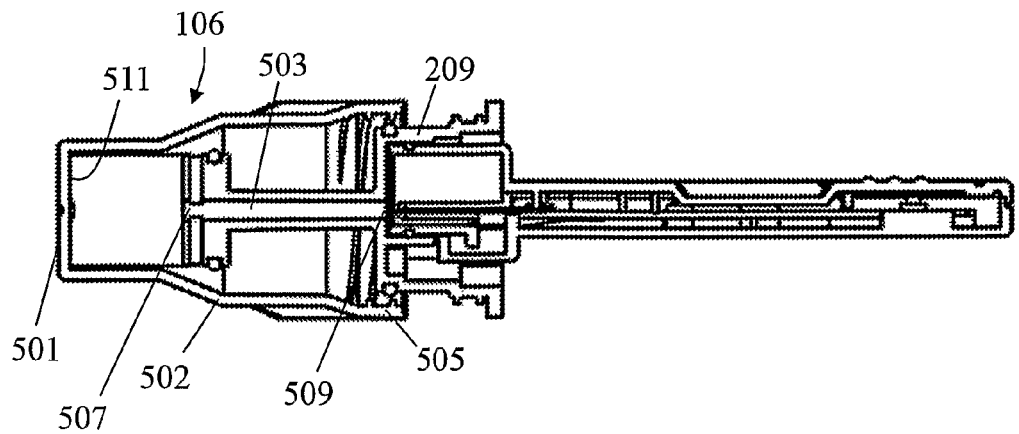
FIG. 5 is a cross-sectional view of a device of the invention in the first position, where the absorbent material (here a sponge) is uncompressed.
Figure 6:
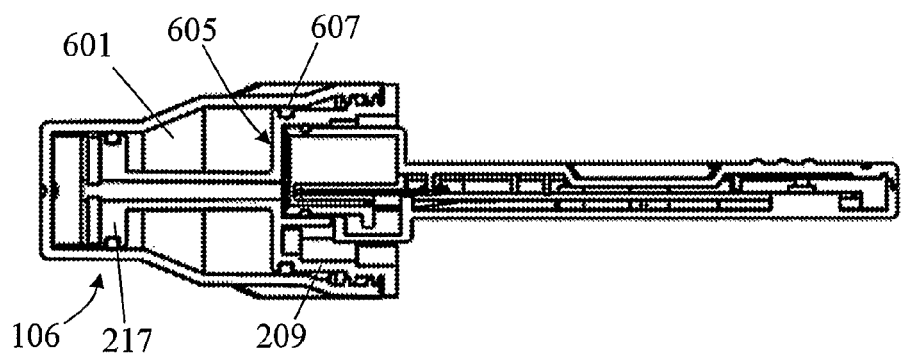
FIG. 6 is a cross-sectional view of a device of the invention in the second, locked position, where the absorbent material is compressed.
Figure 7:
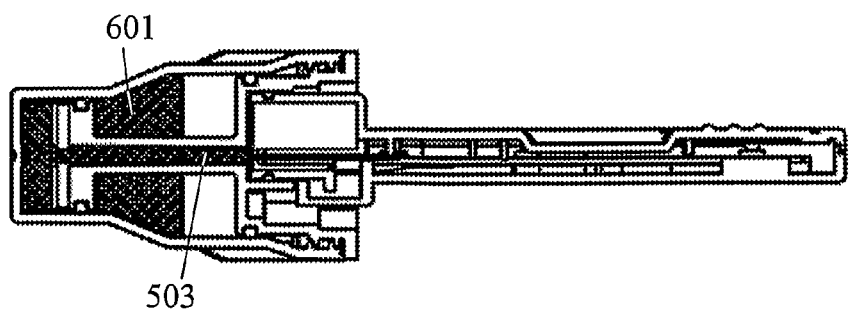
FIG. 7 is a cross-sectional view of a device of the invention illustrating the sample storage area in the device.

In the embodiment depicted the receiving cup 106 has a substantially barrel shape having a bottom portion 501 and a flared, circumferential side wall 502. As illustrated in FIGS. 5-7, the bottom portion 501 is suitable for receiving the absorbent member 213 and the side wall 502 is suitable for receiving the sample collector base 209. In this embodiment receiving threads 505 are provided inside the open end of the side wall 502 and which mate with the screw threads 227 on the base 209 of the sample collector 102. Therefore, in one embodiment the sample collector 102 is screwed into the receiving cup 106 and placed in the locked position by engaging the screw threads of the sample collector base with the receiving threads of the receiving cup.

In embodiments using "screw threads" and "receiving threads," the screw threads can be inserted into the receiving threads to fasten the two components together in the locked position. Alternatively, the receiving cup can have screw threads and the sample collector can have the receiving threads. But in other embodiments other methods can be used to fasten the sample collector and receiving cup in the locked position. For example, a snap fit connection or other structures that place the sample collector and receiving cup into a locked position can be used. In other embodiments the receiving cup can fit snuggly over the base of the sample collector and thereby form a seal through which fluid sample cannot leak from the device. Sealing structures such as O-rings are used in some embodiments, but a seal through which fluid sample cannot leak can be formed even without use of such structures. In some embodiments the sample collector and receiving cup will be reversibly fastened so that the device can be placed into a locked position and later moved to an unlocked position. But in other embodiments the fastening need not be reversible, only that sample can be conveniently withdrawn from the device for confirmation testing.

One embodiment of the locked position of the device is illustrated in FIG. 6. When in the locked position, the open end of the receiving cup 106 is covered or obstructed by the sample collector base 209. An enclosed space 601 for storing fluid is present in the receiving cup and in one embodiment is defined between the inner surface 603 of the plunger head 217 and the interior surface 605 of the sample collector base 209. In one embodiment, the receiving cup is sealed from fluid communication with the exterior of the device by a sealing means, such as an O-ring 607 provided between the circumferential outer surface of the sample collector base 209 and the inner surface of the side wall 502. But in other embodiments, the mechanism for sealing the device can be other parts that fit snuggly together, other materials that accomplish a sealing by blocking fluid movement between the interior and exterior of the device (e.g., plastic, rubber materials), or by an O-ring provided in another location, such as between the circumferential outer surface of the plunger head and the inner surface of the side wall.

By a "locked" position is meant that the sample collector and receiving cup are fastened together into a unitary device so that fluid sample does not leak from the device, and the device can be safely and conveniently transported for confirmation testing. In one embodiment, the sample collector has screw threads and the receiving cup has receiving threads that are engaged to join the sample collector and receiving cup and seal the fluid sample within the device. In another embodiment the sample collector can have the receiving threads and the receiving cup can have the screw threads. In still other embodiments the locked position can be achieved through other structures. For example, tabs that snap together to join the two components, or other parts that fit snuggly and hold the two components together. In one embodiment the absorbent member of the device is compressed when the sample collector is in the locked position.

With respect to FIG. 5, an assembled sample collector is depicted being inserted into the receiving cup 106. FIG. 5 also illustrates that in this embodiment the extender 215 is hollow in its central area to provide a passageway 503 for fluid from the absorbent member to the test element (through the bibulous material). The passageway 503 has an inlet 507 for receiving fluid from the absorbent member 213 and an outlet 509 for discharging fluid to a test element. In other embodiments other structures can be used to allow for sample to enter the test element. For example, the bibulous material may be extended to reach the sample in the device, or other channels can be utilized to carry sample fluid to the test element.

In one embodiment, a sampling hole 229 is present in the side wall of the receiving cup and can be covered by and sealed with a plug 231 during testing of the sample and transportation of the device. When the device is received at a clinical testing facility, the plug 231 can be removed and the operator can remove a sample for confirmation testing. In one embodiment the sample is conveniently removed by the operator using a pipette or other sampling device when the plug is opened. The device conveniently remains in the locked position but still allows for withdrawal of sample fluid. In one embodiment a plurality of ribs 233 are formed around the side wall to reinforce it and to provide ease in gripping the receiving cup portion of the device.

Describing a use of the embodiment of the invention depicted in FIGS. 1-7, the absorbent member 213 of the sample collector 102 is placed into the mouth of a test subject and is easily supported in the mouth by use of the plunger head 217. The absorbent member is thus filled with saliva. Then, as shown in FIG. 5, the sample collector 102 is inserted into the receiving cup and positioned in a first position within the receiving cup, in which the absorbent member is uncompressed and filled with saliva sample. Its proximal end 301 may or may not abut against the bottom surface 511 of the receiving cup. The sample collector 102 is moved axially into the receiving cup and rotated to a second, locked position. In this embodiment, when the device is in the locked position the absorbent member is compressed and the screw threads 227 of the sample collector base 209 are engaged with the receiving threads 505 of the receiving cup 106. In the locked position the sample collector is fastened into the receiving cup, and fluid does not leak from the device. Fluid sample collected in the absorbent member is extracted by the mechanical pressure of compressing the absorbent member when the sample collector is placed into the locked position. This causes a portion of fluid sample to flow through the passageway 503 and onto the bibulous material 225 of the test element 207. After a period of minutes necessary for the assay to be completed, the presence or amount of analyte in the fluid sample is determined. When the absorbent material 213 is compressed, another portion of the fluid sample is squeezed into the closed space 601 for confirmation testing at a later time, for example at a clinical testing facility. For confirmation testing, the plug 235 is removed and the stored fluid sample is easily recovered through the sampling hole 229 using a pipette 401.

Figure 8:
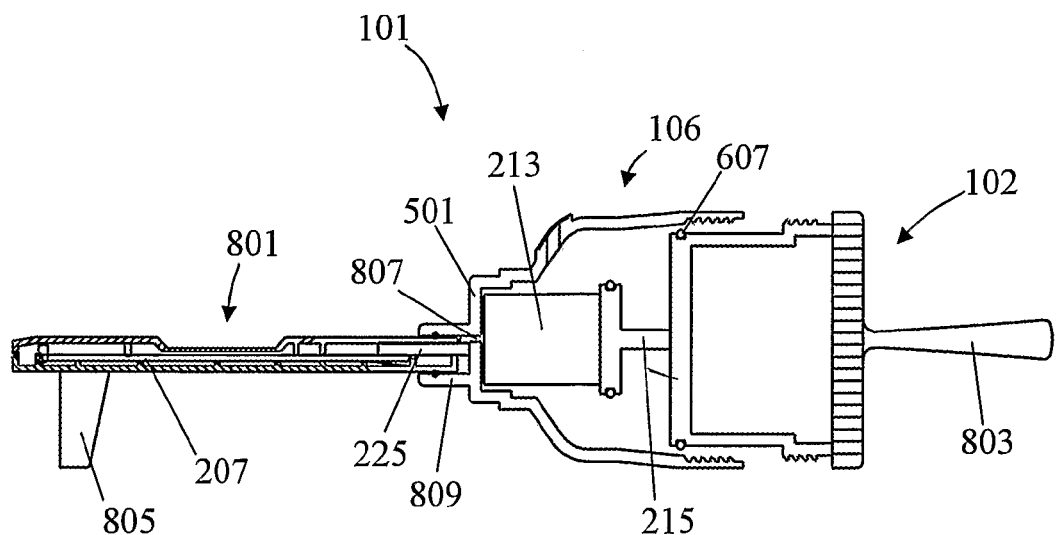
FIG. 8 is a cross-sectional view of a device of the invention showing the sample collector in the first position, where the absorbent material (here a sponge) is uncompressed.
Figure 9:
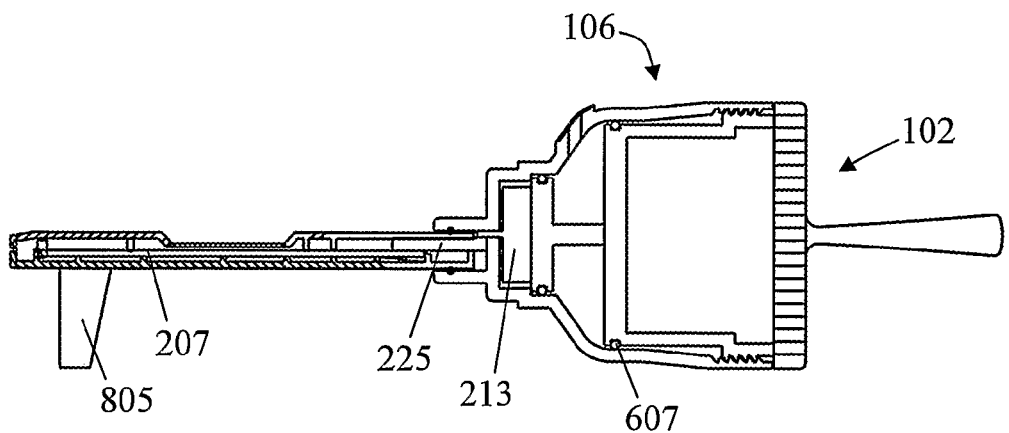
FIG. 9 is a cross-sectional view of a device of the invention, showing the sample collector in the second, locked position, where the absorbent material (here a sponge) is compressed.

In FIGS. 8 and 9, another embodiment of the invention is illustrated. In this embodiment the test element holder is directly connected to the receiving cup 106 and is not attached to the sample collector. With reference to FIG. 9, the device 100 comprises a sample collector 102 and a receiving cup 106, with the test element holder 801 extending from the receiving cup. The sample collector 102 contains an absorbent member 213. In one embodiment a handle 803 for manually gripping the sample collector 102 is present on the test element holder. In this embodiment the extender is not hollow, and fluid does not pass through a passageway in the extender to arrive at the test element. Rather, fluid sample passes through the channel 807 in the bottom portion 501 of the receiving cup 106. By two structures being "directly connected" is meant that contact exists between at least some portion of the two structures.

In different embodiments a test element handle 805 can also be present on the test element holder 801. In cross-sectional view of FIG. 9, there is a channel 807 present in the bottom portion 501 of the receiving cup 106. In one embodiment a socket 809 is present on the receiving cup suitable for attaching and holding the test element holder 801 in place on the receiving cup is provided on the bottom portion 501. Referring to FIG. 9, in use the test element holder 801 is inserted in the socket 809 and fixed in place so that the absorbent material 213 is placed into fluid communication with the bibulous material 225, and therefore also at least one test element 207 through the channel 807.

EXAMPLE 1

One hundred thirty saliva samples were collected from one hundred thirty test subjects using a sample collector described herein, by placing the sample collector in the mouth of the subject until it was filled with saliva. After loading with sample, the sample collectors were placed into a receiving cup of the device, the absorbent member compressed, and the sample extracted. Thirty of the samples were spiked with a mixture of drugs of abuse, including amphetamines, cocaine, methamphetamine, opiates, THC, and phencyclidine. The sample collector had screw threads and the receiving cup receiving threads. The device was then placed into the locked position to retain sample within the device, and the assay was automatically begun. After 10 minutes, the result was recorded as positive or negative. Each device was configured with two test strips, which each tested for three drugs of abuse. Between the two test strips, the following six drugs of abuse were tested for: amphetamines (AMP), cocaine (COC), methamphetamine (MET), opiates (OPI), tetra-hydrocannabinol (THC), and phehcyclidine (PCP).

The one hundred samples that had not been spiked with a drug of abuse all tested negative. The thirty samples that had been spiked with the mixture of drugs all provided a positive result for each of the six drugs, with the exception that only 28 of the 30 samples tested positive for THC.

A confirmation test using a well-accepted procedure was then performed on these samples. In the confirmation test, all thirty samples tested positive for all six drugs.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A device for detecting the presence or amount of an analyte in a fluid sample comprising:
   a sample collector comprising a compressible absorbent member for collecting the fluid sample, at least one test element having reagents for detecting the presence or amount of the analyte in the fluid sample, and an extender element positioned between the absorbent member and the test element and defining an elongated fluid passageway between the absorbent member and the test element; and
   a receiving cup reversibly coupled to the sample collector for receiving and holding the sample collector within the receiving cup, the receiving cup having a sidewall, a first open end for engaging the sample collector, a second end opposing the first open end, and a sampling hole through the wall separate from the open end, the sample collector having a first position and a second, locked position within the receiving cup, the compressible absorbent member being uncompressed in the first position and being compressed and held within the cup in the second, locked position, and wherein transition from the first position to the second position causes extraction of the fluid sample from the compressible absorbent member and flow of a portion of the fluid sample along the elongated fluid passageway to the test element via a compressive force generated between the extender element and the second end of the receiving cup.

2. The device of claim 1 wherein the sample collector comprises a test element holder housing the test element.

3. The device of claim 1 wherein an absorbent pad is positioned between the extender element and the test element and transfers fluid from the passageway to the test element.

4. The device of claim 1 wherein the sample collector comprises circumferential screw threads, and the receiving cup comprises circumferential receiving threads.

5. The device of claim 4 wherein the screw threads and receiving threads are engaged when the sample collector is in the second, locked position.

6. The device of claim 5 wherein the receiving cup is sealed from fluid communication with the exterior when the sample collector is in the second, locked position.

7. The device of claim 1 wherein the sample collector and the receiving cup are joined by a snap fit connection when the sample collector is in the second, locked position.

8. The device of claim 1 wherein the absorbent member is a sponge suitable for placing in the mouth of a test subject, and the fluid sample is saliva.

9. The device of claim 2 wherein the sample collector comprises a flattened handle for manually gripping the sample collector.

* * * * *